(12) United States Patent
Min et al.

(10) Patent No.: US 12,229,464 B2
(45) Date of Patent: Feb. 18, 2025

(54) AMPLIFICATION DATA DISPLAY METHOD AND DEVICE

(71) Applicant: SEEGENE, INC., Seoul (KR)

(72) Inventors: Kyung Hyun Min, Guri-si (KR); Gyeong Mo Gu, Goyang-si (KR)

(73) Assignee: SEEGENE, INC., Seoul (KR)

( * ) Notice: Subject to any disclaimer, the term of this patent is extended or adjusted under 35 U.S.C. 154(b) by 0 days.

(21) Appl. No.: 16/651,472

(22) PCT Filed: Aug. 2, 2018

(86) PCT No.: PCT/KR2018/008810
§ 371 (c)(1),
(2) Date: Mar. 27, 2020

(87) PCT Pub. No.: WO2019/066238
PCT Pub. Date: Apr. 4, 2019

(65) Prior Publication Data
US 2020/0264824 A1 Aug. 20, 2020

(30) Foreign Application Priority Data
Sep. 28, 2017 (KR) .................. 10-2017-0125907

(51) Int. Cl.
*G06F 3/0486* (2013.01)
*G06F 3/14* (2006.01)
(52) U.S. Cl.
CPC .......... *G06F 3/1407* (2013.01); *G06F 3/0486* (2013.01)
(58) Field of Classification Search
CPC .............................. G06F 3/0486; G06F 3/1407
See application file for complete search history.

(56) References Cited

U.S. PATENT DOCUMENTS 9,390,227 B2   7/2016  Janaway et al.
2006/0004526 A1   1/2006  Hadd et al.
(Continued)

FOREIGN PATENT DOCUMENTS

EP          2407557 A2   1/2012
KR      20100102560 A   9/2010
(Continued)

OTHER PUBLICATIONS

Office Action issued in corresponding KR Patent Application No. 10-2020-7011629 dated May 17, 2021.
(Continued)

*Primary Examiner* — Nelson M Rosario
*Assistant Examiner* — Scott D Au
(74) *Attorney, Agent, or Firm* — Studebaker & Brackett PC

(57) ABSTRACT

An amplification data display method according to the present invention comprises the steps of: displaying a plate display area and an integrated data display area; displaying, in the plate display area, plates where nucleic acid amplification reactions have been performed; and displaying amplification data in the integrated data display area, wherein: two or more plates are displayed in the plate display area; each of the plates includes a plurality of reaction wells; the amplification data are generated from the reaction wells by the nucleic acid amplification reactions; and amplification data for a plurality of reaction wells selected from the reaction wells of two or more of the displayed plates are displayed in the integrated data display area.

17 Claims, 12 Drawing Sheets

(56) References Cited

U.S. PATENT DOCUMENTS

| | | | |
|---|---|---|---|
| 2011/0039274 A1 | 2/2011 | Ludowise | |
| 2012/0135394 A1* | 5/2012 | Kim | B03C 1/288 |
| | | | 435/5 |
| 2017/0226563 A1 | 8/2017 | Chun et al. | |
| 2018/0190386 A1* | 7/2018 | Yoshikawa | G16H 40/40 |

FOREIGN PATENT DOCUMENTS

| | | |
|---|---|---|
| KR | 20110008261 A | 1/2011 |
| KR | 20170051539 A | 5/2017 |

OTHER PUBLICATIONS

Extended European Search Report issued in corresponding EP Patent Appication No. 18862369.8 dated May 20, 2021.

"LightCycler® 96 Real-Time PCR System: Super Capabilities Are Now Within Your Reach," dated Jan. 1, 2013 by Roche Diagnositcs Gmbh.

\* cited by examiner

FIG.10

Integrated Data Display Area(1010)

| | First Plate | Second Plate | Third Plate | First Integrated Data | | Second Integrated Data |
|---|---|---|---|---|---|---|
| ID | | plate | well | Ct | | P/N |
| 001 | | 1 | A1 | 25 | | Positive |
| 001 | | 2 | B3 | 28 | | Positive |
| 001 | | 3 | C6 | - | | Negative |
| 002 | | 1 | A2 | - | | Negative |
| 002 | | 2 | B4 | 24 | | Positive |

AMPLIFICATION DATA DISPLAY METHOD AND DEVICE

TECHNICAL FIELD

The present disclosure relates to a method of and a apparatus for displaying amplification data generated by nucleic acid amplification reactions.

BACKGROUND ART

A polynucleotide chain reaction (PCR), most widely used for nucleic acid amplification reactions, includes repeated cycles of denaturation of double-stranded deoxyribonucleic acid (DNA), followed by oligonucleotide primer annealing to a DNA template and primer extension by a DNA polymerase (Mullis, et al., U.S. Pat. Nos. 4,683,195, 4,683,202, and 4,800,159; and Saiki, et al., (1985) Science 230, 1350-1354).

Real-time PCR is a PCR-based technology for detecting a target nucleic acid in a sample. To detect a specific target nucleic acid, a signal generator emitting a fluorescent signal detectable in proportion to the amount of the target nucleic acid is used. The fluorescent signal, the intensity of which is proportional to the amount of the target nucleic acid, is detected at each measurement point (cycle). In this manner, a data set including measurement points and signal values at the measurement points is obtained, and an amplification curve or amplification profile curve on which the intensities of the fluorescent signal at the measurement points are plotted is obtained from the data set.

In general, the amplification curve of the real-time PCR is divided into a baseline region, an exponential phase, and a plateau phase. The exponential phase is a region in which emitted fluorescent signals increase in proportion to increases in PCR amplification products. The plateau phase is a region in which no increases in fluorescent signals appear due to saturated increases in PCR amplification products and the saturated emission of fluorescent signals. The baseline phase refers to a region in which fluorescent signals remain constant without changes at an early stage of the reaction. In the baseline phase, PCR amplification products may be insufficient such that fluorescent signals are not detectable. Thus, most fluorescent signals obtained in the baseline phase are fluorescent signals of a reaction sample or a background signal, i.e. a fluorescent signal, from a measurement system, rather than fluorescent signals generated by the amplification of a target analyte.

Real-time PCR reaction devices of the related art (e.g. CFX96 available from Bio-rad Laboratories, Inc., QS5 available from Thermo Fisher Scientific Inc.) provide a window in which data sets obtained from reaction wells included in a plate may be exhibited in the form of an amplification curve or a table. However, such a window provided by the real-time PCR reaction devices of the related art only allows data sets obtained from reaction wells included in a single plate to be exhibited but may not exhibit information obtained from two or more reaction wells included in different plates in an integrating manner. Since the real-time PCR reaction devices of the related art may only display data regarding a single plate in a single window, data regarding another plate are displayed in a new window. Accordingly, it may be difficult for a user to simultaneously review or compare data sets or amplification curves included in different plates, which is problematic. For example, in a case in which two or more samples of a single patient are included in different plates, the user must check two or more windows to review data of the samples of the patient.

DISCLOSURE

Technical Problem

Accordingly, the present disclosure provides a method and apparatus for displaying amplification data of reaction wells included in different plates in an integrating manner.

Technical Solution

A amplification data display method according to the present disclosure includes: displaying a plate display area an integrated data display area, wherein the plate display area displays plates in which nucleic acid amplification reactions have been performed, and the integrated data display area displays amplification data; displaying two or more plates in the plate display area, wherein each of the plates includes a plurality of reaction wells, and the amplification data are generated from the reaction wells by the nucleic acid amplification reactions; and displaying the amplification data of the plurality of reaction wells selected from the two or more plates among the plates displayed in the integrated data display area.

According to an example, in the displaying of the amplification data, the amplification data of the plurality of selected reaction wells may be displayed on at least one of a graph and a table.

According to an example, the displaying of the amplification data may be performed by receiving an operation of dragging and dropping the selected reaction wells to the integrated data display area.

According to an example, in the displaying of the amplification data, the amplification data of the reaction wells selected in accordance with set selection criteria may be displayed on at least one of a graph and a table.

According to an example, in the displaying of the amplification data, the amplification data may be sorted and displayed by a sorting method using identification information of the reaction wells included in different plates.

According to an example, images of the plates may be displayed in the plate display area, and the reaction wells in the plates may be displayed as icons or using texts indicating identification information regarding the reaction wells.

According to an example, the amplification data may include at least one from among a set of cycle numbers and signal values, a signal value in a specific cycle, a positive/negative result, and a cycle threshold value.

According to an example, the plate display area may include an icon used to add a plate to be displayed, or the integrated data display area may include an icon used to add displaying of other amplification data.

A data processing apparatus according to the present disclosure includes: a memory; a display apparatus; and a processor, wherein the processor displays a plate display area and an integrated data display area on the display apparatus, wherein the plate display area displays plates in which nucleic acid amplification reactions have been performed, and the integrated data display area displays amplification data; the processor displays two or more plates in the plate display area on the display apparatus, wherein each of the plates includes a plurality of reaction wells, and the amplification data are generated from the reaction wells by the nucleic acid amplification reactions; and the processor displays the amplification data of the plurality of reaction wells, selected from the two or more plates among the plates displayed in the integrated data display area, on the display apparatus.

According to an example, the processor may display the amplification data of the plurality of selected reaction wells on at least one of a graph and a table.

According to an example, the displaying of the amplification data may be performed by receiving an operation of dragging and dropping the selected reaction wells to the integrated data display area.

According to an example, the processor may display the amplification data of the reaction wells, selected in accordance with set selection criteria, on at least one of a graph and a table.

According to an example, the processor may display the amplification data by sorting the amplification data by a sorting method using identification information of the reaction wells included in different plates.

According to an example, images of the plates may be displayed in the plate display area, and the reaction wells in the plates may be displayed as icons or using texts indicating identification information regarding the reaction wells.

According to an example, the amplification data may include at least one from among a set of cycle numbers and signal values, a signal value in a specific cycle, a positive/negative result, and a cycle threshold value.

According to an example, the plate display area may include an icon used to add a plate to be displayed, or the integrated data display area may include an icon used to add displaying of other amplification data.

A non-transitory recording medium stores a computer executable program. The program includes: displaying a plate display area an integrated data display area, wherein the plate display area displays plates in which nucleic acid amplification reactions have been performed, and the integrated data display area displays amplification data; displaying two or more plates in the plate display area, wherein each of the plates includes a plurality of reaction wells, and the amplification data are generated from the reaction wells by the nucleic acid amplification reactions; and displaying the amplification data of the plurality of reaction wells selected from the two or more plates among the plates displayed in the integrated data display area.

Advantageous Effects

According to the present disclosure, amplification data of reaction wells included in a plurality of plates may be integrated and displayed as selected by a user.

According to the present disclosure, amplification data of reaction wells included in a plurality of plates may be displayed in accordance with selection criteria or sorting criteria.

DESCRIPTION OF DRAWINGS

FIGS. 9 and 10 are diagrams illustrating a second graphic user interface (GUI), by which the amplification data display method according to an embodiment is performed, and the amplification data display method using the second GUI;

MODE FOR INVENTION

Figure 1:
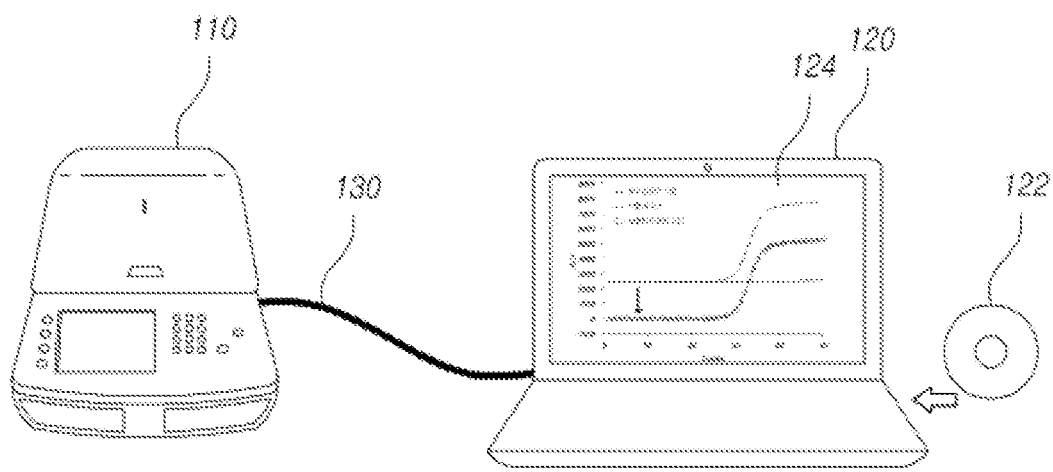
FIG. 1 illustrates an amplification apparatus and an amplification data display apparatus according to an embodiment.

Hereinafter, the present disclosure will be described in detail with respect to embodiments. The embodiments according to the present disclosure are intended to fully convey the present disclosure, and those having ordinary knowledge will appreciate that the scope of the present disclosure is not limited by the embodiments.

The term "nucleic acid amplification reaction" as used herein includes a variety of polynucleotide chain reactions (PCRs) based on a polymerase chain reaction. For example, the nucleic acid amplification includes quantitative PCR, digital PCR, asymmetric PCR, reverse transcriptase PCR (RT-PCR), differential display PCR (DD-PCR), nested PCR, arbitrary priming PCR, multiplex PCR, SNP genome typing PCR, and the like.

The term "plate" as used herein refers to a reference unit in which amplification reactions are performed in a PCR apparatus, and means a basic unit in which data generated after the amplification reaction are stored. Different plates may be plates in which amplification reactions are performed at different times using the same amplification apparatus, or plates for which amplification reactions are performed by different amplification apparatus at the same time.

The plate includes a plurality of reaction wells. The plate may include N×M number of reaction wells. Typically, the plate includes 12×8 or 8×12 number of reaction wells. The reaction wells of the plate may be tubular structures integrated with or detachable from the plate. The plate may have a rectangular shape, but may have a variety of shapes, such as a circle, a trapezoid, or a diamond, including one or more reaction well, in addition to the rectangular shape.

The wells of the plate contain samples to be analyzed or reagents necessary for nucleic acid amplification reactions.

The term "target analyte" as used herein refers to target nucleic acid molecules (e.g. deoxyribonucleic acid (DNA) and ribonucleic acid (RNA)).

Target nucleic acid molecules may include, for example, nucleic acids from prokaryotic cells, nucleic acids from eukaryotic cells (e.g., protozoans, parasitic animals, fungi, yeasts, higher plants, lower animals, higher animals including mammals and humans), nucleic acids from viruses (e.g., the herpes virus, a human immunodeficiency virus (HIV), an influenza virus, the Epstein-Barr virus, a hepatitis virus, the poliovirus), and viroid nucleic acids. Target nucleic acid molecules include not only natural nucleic acid sequences, but also artificial nucleic acid sequences, and may include known sequences or unknown sequences. The nucleic acid sequences may be naturally induced, recombinantly produced, or chemically synthesized. According to an implementation of the present disclosure, target nucleic acid molecules are nucleic acid sequences including nucleotide variations.

The term "sample" as used herein includes biological samples (e.g. cells, tissues, and body fluids) and abiotic samples (e.g. foods, water, and soil). Examples of the biological samples are viruses, saliva, sputum, a swab (e.g. a nasopharyngeal swab, a nasal swab, a throat swab, a cervical swab, a urethral swab, vaginal swab, a rectal swab, or the like), aspirate (e.g. nasopharyngeal aspirate), milk, urine, stool, eye fluid, semen, brain extracts, spinal fluid, cerebrospinal fluid, synovial fluid, thymus fluid, branchial lavage, bronchoalveolar lavage, ascites, amniotic fluid, and liquid based cytology (LBC) samples (e.g. ThrinPrep™ and Surepath™). In a case in which the target analyte is the target nucleic acid molecule, the samples may be subjected to a nucleic acid extraction process known in the art to which the present disclosure relates (see Sambrook, J. et al., Molecular Cloning: A Laboratory Manual, 3rd ed. Cold Spring Harbor Press (2001)). The nucleic acid extraction process may vary depending on the types of samples. In addition, in a case in which the extracted nucleic acid is RNA, a reverse transcription process for synthesizing cDNA may be added (see Sambrook, J. et al., Molecular Cloning: A Laboratory Manual, 3rd ed. Cold Spring Harbor Press (2001).

The term "signal-generating reaction" as used herein refers to a reaction of generating a signal depending on the properties of the target analyte in a sample, e.g. the activity, amount or presence (or absence), in particular, the presence (or absence), of the target analyte. According to an implementation of the present disclosure, the signal-generating reaction is a genetic analysis process. The signal-generating reaction is accompanied with signal changes. The term "signal" as used herein refers to a measurable output.

The size, change, or the like of the signal serves as an indicator qualitatively or quantitatively indicating the properties, in particular, the presence or absence, of the target analyte. A frequently used indicator is fluorescence intensity. Such a change in the signal includes the appearance or disappearance of the signal and not only an increase but also a decrease in the size of the signal.

A variety of methods of providing signals using a signal-generating means able to generate signals depending on the presence of the target nucleic acid molecule in the nucleic acid amplification process are known. In the present disclosure, any method may be used.

A data set obtained through amplification reactions includes an amplification cycle.

In a case in which a predetermined reaction having a predetermined process is repeated or a reaction occurs is repeated for a predetermined time interval, the term "cycle" refers to a single unit of such repetition.

For example, in the PCR, a single cycle refers to a reaction including denaturation of a nucleic acid, hybridization or annealing of the nucleic acid with a primer, and primer extension. In this case, a change in a predetermined condition is an increase in the number of repetitions, and the repeating unit in reactions, including a series of the above-described operations, is set to be a single cycle.

In the present disclosure, the amplification of target nucleic acid molecules may be performed by a variety of known methods. For example, such methods include polymerase chain reaction (PCR), strand displacement amplification (SDA), transcription-mediated amplification, nucleic acid sequence-based amplification (NASBA), and the like.

According to an implementation of the present disclosure, the signal-generating means includes fluorescence intensity. More specifically, the signal-generating means includes a fluorescent single label or an interactive dual label including a donor molecule and an acceptor molecule (e.g. fluorescent reporter molecules and quencher molecules).

In a case in which the fluorescent label is used, a signal value may be expressed as a relative fluorescence unit (RFU) value.

According to an implementation of the present disclosure, the amplification reaction amplifies a signal with the amplification of the target analyte (in particular, target nucleic acid molecule) being accompanied therewith. According to an implementation of the present disclosure, the amplification reaction is performed by the PCR, in particular, the real-time PCR.

The data set obtained from the signal-generating reaction includes a plurality of data points including the cycles of the signal-generating reaction and the signal values in the cycles.

The term "signal value" as used herein refers to a numerical value obtained by quantifying the level (e.g. intensities) of a signal actually measured in a signal-generating reaction, in particular, a cycle of amplification reactions or a variant value of the numerical value.

The term "data point" as used herein refers to a coordinate value including a cycle and a signal value. The term "data" refers to any type of information of which the data set is constituted. For example, individual cycles and signal values of the amplification reactions are data.

The data points obtained from the signal-generating reaction, in particular, the amplification reactions may be indicated with coordinate values expressible on a two-dimensional orthogonal coordinate system. In the coordinate values, the X-axis indicates the number of corresponding cycles, while the Y-axis indicates signal values measured from the corresponding cycles or processed signal values thereof.

The term "data set" as used herein refers to a set of such data points. For example, the data set may be a set of data points directly obtained through amplification reactions performed in the presence of the signal-generating means or a variant data set obtained by varying the data set. The data set may be a portion or the entirety of a plurality of data points obtained by the amplification reactions or a portion or a plurality of variant data points.

In addition, the data set according to the present disclosure may be a data set obtained by processing a plurality of data sets. In a case in which a plurality of target analytes are analyzed using a single reaction vessel, a data set regarding the plurality of target analytes may be obtained, in some cases, by processing data sets obtained from reactions performed in the single reaction vessel. For example, a data set regarding a plurality of target analytes obtained from a single reaction vessel may be obtained by processing a plurality of data set obtained from signals measured at different temperatures.

The data set may be plotted, by which an amplification curve may be obtained.

According to an implementation of the present disclosure, the method of the present disclosure further includes an operation of performing a signal-generating reaction to obtain a data set.

According to an implementation of the present disclosure, the data set regarding the target analyte obtained from the signal-generating reaction is a data set indicating the presence or absence of the target analyte. The expression "determination of the presence or absence of a target analyte in a sample" refers to qualitatively or quantitatively determining the target analyte in the sample.

FIG. 1 illustrates an amplification apparatus and an amplification data display apparatus according to an embodiment. Referring to FIG. 1, an analysis system includes an amplification apparatus 110 and a data processing apparatus 120. The analysis system may determine the presence or absence of a target analyte in a sample and display the analysis result to a user. The presence of the target analyte in the sample may be expressed as positive, while the absence of the target analyte in the sample may be expressed as negative.

The amplification apparatus 110 is a apparatus performing nucleic acid amplification nucleic acid amplification. The amplification apparatus 110 may repeatedly perform an operation of increasing and decreasing the temperature of samples. The amplification apparatus 110 may obtain a data set by measuring signals generated from the samples in every cycle.

The amplification apparatus 110 may perform nucleic acid amplification reactions for a single plate. The amplification apparatus 110 may perform nucleic acid amplification reactions for a plurality of plates in different times. In addition, a plurality of amplification apparatus 110 may simultaneously perform nucleic acid amplification reactions for a plurality of plates. The amplification apparatus 110 obtains a data set from the samples by performing the nucleic acid amplification reactions.

The data processing apparatus 120 may generate an amplification curve using the data set. The data processing apparatus 120 may remove noise from the data set and generate the amplification curve using the noise-removed data set. The data processing apparatus 120 may analyze data generated from reaction wells of the plate to determine each sample to be positive or negative, a cycle threshold (Ct) value, a signal value (e.g. an RFU value) in a specific cycle, and the like.

Operations of, for example, removing noise from the data set, generating the amplification curve, analyzing the data set, and the positive/negative determination may be performed by the amplification apparatus 110. Such operations may be performed by two or more data processing apparatuses.

The amplification apparatus 110 and the data processing apparatus 120 or data processing apparatuses among a plurality of data processing apparatuses may be connected via a cable 130 or a wireless medium to transmit information to each other. In addition, data may be exchanged via a recording medium.

The data processing apparatus 120 may determine the presence or absence of the target analyte in the sample by analyzing the data set, detect data regarding the samples, and store the data in a memory.

The data processing apparatus 120 includes a display apparatus 124. The display apparatus 120 may display noise-removed data, an amplification curve, or the like. In addition, the display apparatus 124 may display the presence or absence of the target analyte in each sample and display a detection result of each sample, such as a Ct value or a signal value (e.g. an RFU value).

The data processing apparatus 120 may read data from a recording medium 122. The recording medium 122 may store, for example, a data set or a program used in the data processing apparatus 120. The recording medium 122 may be a compact disc (CD), a universal serial bus (USB) memory, or the like.

The data processing apparatus 120 may be a computer, a smartphone, a tablet computer, a wearable apparatus, or the like.

Figure 2:
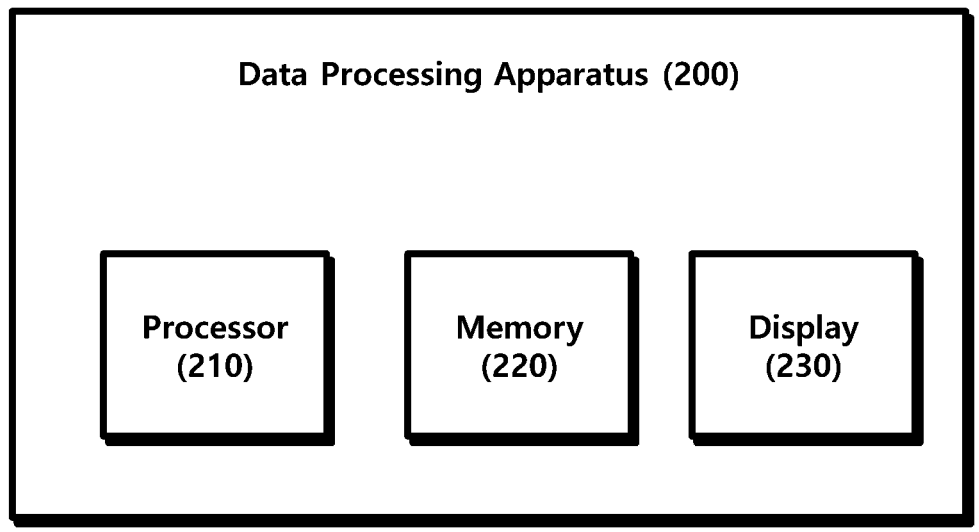
FIG. 2 is a configuration diagram illustrating a data processing apparatus according to an embodiment.

FIG. 2 is a configuration diagram illustrating a data processing apparatus according to an embodiment. Referring to FIG. 2, the data processing apparatus 200 includes a processor 210, a memory 220, and a display apparatus 230.

The memory 220 stores data. The memory 220 may store data received from the amplification apparatus 110 or data processed by the processor 210. For example, the memory 220 may store data sets, noise-removed data sets, amplification curves, Ct values, signal values (e.g. RFU values), and the like. The memory 220 may store data for each plate or strip. The memory 220 may store data regarding a plurality of plates and integrated data generated on the basis of the data regarding the plurality of plates. The data regarding the plates includes numbers or letters by which plates are identified, information recorded about the plates, or data regarding reaction wells included in the plates. The information recorded about the plates includes various types of information, such as dates, times, or methods, regarding the performance of amplification reactions. The data regarding the reaction wells includes a data set, a noise-removed data set, Ct values, signal values, and the like regarding each of the reaction wells.

Although the memory 220 is illustrated as a component separate from the processor 210 in FIG. 2, the memory 220 and the processor 210 may be implemented as a single apparatus. For example, the memory 220 may be a storage, such as a cache, provided inside of the processor 210.

The processor 210 may write data in the memory 220 or read data from the memory 220. The processor 210 may display data on the display apparatus 230 by controlling the display apparatus 230. For example, the processor 210 may display a table, a graph, texts, or the like on the display apparatus 230.

Although the data processing apparatus 200 is illustrated as including a single processor 210 in FIG. 2, the data processing apparatus 200 may include one or more processors 210.

The display apparatus 230 may display a graph, a table, texts, or the like under the control of the processor 210. For example, the display apparatus 230 may display a data set, an amplification curve, or the like on a graph. The display apparatus 230 may display plate identification information, reaction well identification information, amplification data, and the like in a table.

Figure 3:
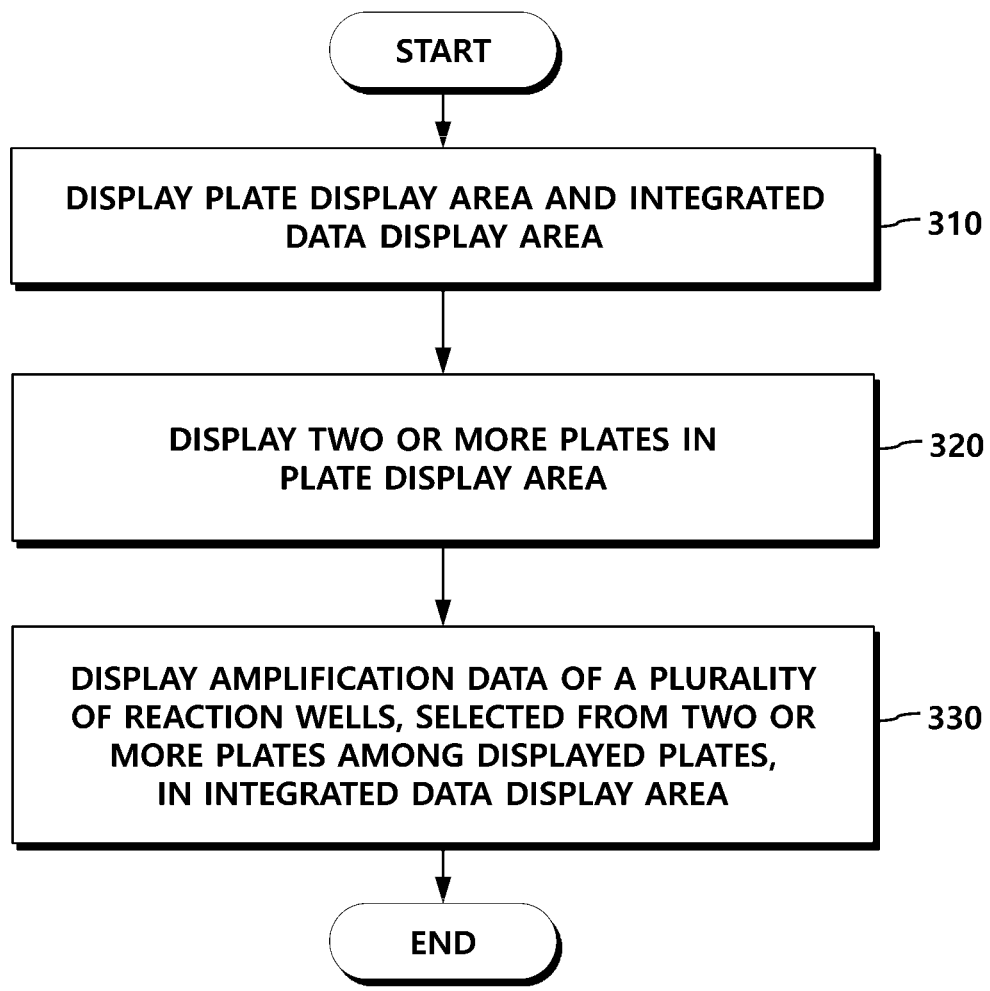
FIG. 3 is a flowchart illustrating an amplification data display method according to an embodiment.

FIG. 3 is a flowchart illustrating an amplification data display method according to an embodiment. Referring to FIG. 3, the data processing apparatus may display amplification data of a plurality of reaction wells selected from two or more plates.

In step 310, the data processing apparatus displays a plate display area and an integrated data display area. The data processing apparatus may display the plate display area and the integrated data display area in a single window. For example, the integrated data display area may be displayed in a left section of the window, while the plate display area may be displayed in a right section of the window.

The plate display area may include two or more tabs, and an area displayed when the corresponding tab is selected is also included in the plate display area.

The plate display area may include two or more separate windows, and an area displayed when the corresponding window is selected is also included in the plate display area.

The plate display area is an area in which a plurality of plates in which nucleic acid amplification reactions have been performed are displayed. That is, after the nucleic acid amplification reactions for the plates have been performed, the result of the nucleic acid amplification reactions for each of the plates is displayed in the plate display area.

The integrated data display area is an area in which amplification data are displayed. The amplification data are generated from each of the reaction wells. For example, the amplification data may a set of signal values about cycles, Ct values, signal values in specific cycle (e.g. RFU values), or the like.

The integrated data displayed in the integrated data display area are amplification data of wells included in different plates. In a case in which a plurality of pieces of integrated data are displayed, each integrated data includes amplification data of two or more wells included in different plates. For example, first integrated data may include amplification data of A1 well in a first plate and amplification data of B2 well in a second plate. Second integrated data may include amplification data of C4 well in the second plate and amplification data of D5 well in a third plate.

The integrated data display area may include two or more tabs, and an area displayed when the corresponding tab is selected is also included in the integrated data display area.

The integrated data display area may include two or more separate windows, and an area displayed when the corresponding window is selected is also included in the integrated data display area.

In step 320, the data processing apparatus displays two or more plates in the plate display area. When a user input is received, the data processing apparatus may display plates selected by the user input. For example, the user may select plates in which the nucleic acid amplification reactions have been completed, and the data processing apparatus displays the plates selected by the user. Each of the plates includes a plurality of reaction wells, and amplification data are generated from the reaction wells due to the nucleic acid amplification reactions.

The plate display area is not intended to simply display a single screen, but may include two or more tabs or two or more separate windows. For example, the data processing apparatus may display two or more plates in divided areas of a single window, display different plates in different tabs, or display different plates in different windows.

The data processing apparatus may display a plate by displaying a plurality of reaction wells of the plate with selectable icons. For example, the data processing apparatus may display 96 reaction wells of a single plate as 96 circles. The data processing apparatus may display the reaction wells with different colors, patterns, shapes, and the like, depending on the characteristics, reaction results, or the like of the reaction wells. For example, the data processing apparatus may display positive reaction wells in white and display negative reaction wells in black.

In step 330, the data processing apparatus displays amplification data of a plurality of reaction wells, selected from two or more plates among the displayed plates, in the integrated data display area. The two or more plates mean different plates. That is, the data processing apparatus may display the amplification data of the two or more reaction wells in the integrated data display area, and the two or more reaction wells are included in the different plates. For example, in a case in which the user has selected a first reaction well and a second reaction well, the first reaction well may be a reaction well included in the first plate, and the second reaction well may be a reaction well included in the second plate. In a case in which the user has selected for reaction wells, first and second reaction wells may be reaction wells included in a first plate, a third reaction well may be a reaction well included in a second plate, and a fourth reaction well may be a reaction well included in a third plate.

The integrated data display area does not simply display a single screen, but may include two or more tabs or two or more windows. Individual integrated data may be displayed in different tabs or different windows, and each integrated data includes amplification data of two or more wells included in different plates. Displaying the amplification data means displaying the amplification data of selected two or more reaction wells in the same area using a graph or displaying the entirety of the amplification data on a single table. A method of displaying the amplification data by the data processing apparatus will be described hereinafter in detail with reference to the drawings.

Figure 4:
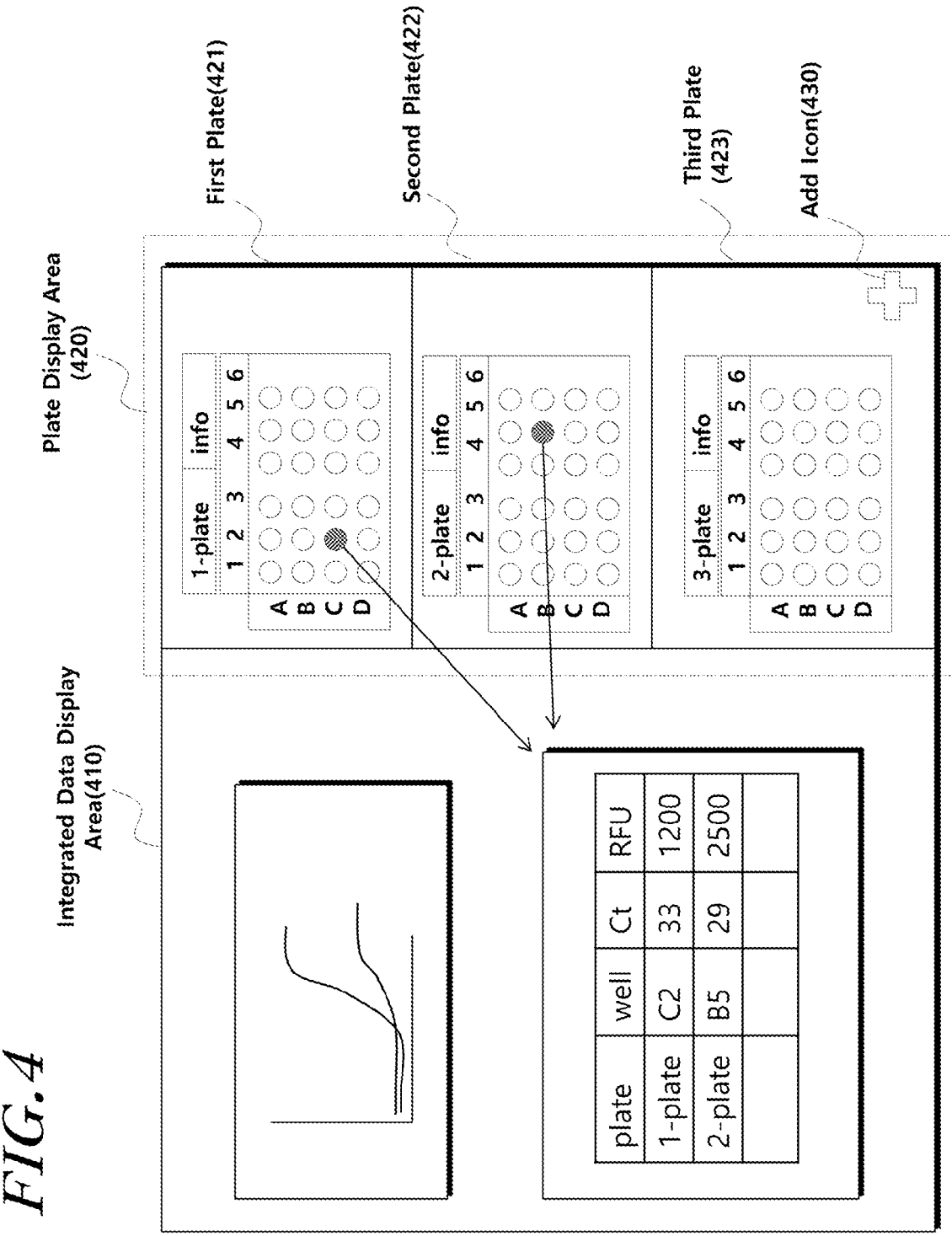
FIG. 4 is a view illustrating a first graphic user interface (GUI), by which the amplification data display method according to an embodiment is performed, and the amplification data display method using the same.

FIG. 4 is a view illustrating a first graphic user interface (GUI), by which the amplification data display method according to an embodiment is performed, and the amplification data display method using the same. Referring to FIG. 4, the data processing apparatus may display amplification data of a plurality of reaction wells, selected from a plurality of plates, in a single integrated data display area 410. The data processing apparatus may display the amplification data, selected from the reaction wells of the plurality of plates, in the integrated data display area 410. For example, FIG. 4 illustrates a case in which two reaction wells displayed black in a plate display area 420 are selected. The data processing apparatus displays the amplification data of C2 well of a first plate 421 and the amplification data of B5 well of a second plate 422 in the integrated data display area 410.

For example, the amplification data of the C2 well of the first plate 421 and the amplification data of the B5 well of the second plate 422 may be amplification data obtainable when analyzing different target analytes using samples collected from a single patient. Thus, even in the case in which amplification reactions for the single patient are performed in different plates, the user may review the amplification data of the single patient by integrating the amplification data.

Since the data processing apparatus displays the plurality of plates on a single screen, the user may easily select the plurality of reaction wells from the plurality of plates. In addition, the data processing apparatus may display the reaction wells of the single patient with icons having the same color or pattern, and the user may easily review and select the reaction wells of the single patient. In addition, the data processing apparatus may display the reaction wells of the single patient with the same number, letter, symbol, or the like.

The data processing apparatus may display the integrated data display area 410 and the plate display area 420 by dividing the integrated data display area 410 and the plate display area 420. The first plate 421, the second plate 422, and a third plate 423 are displayed in the plate display area 420.

Amplification reaction plates to be displayed on plate parts may be designated by the user or may be predetermined. The amplification reaction plates to be displayed may be set (or determined) by a method in which a corresponding plate part recognizes a selection request input of the user, provides a list of amplification reaction plates, and recognizes a selection input of the user.

Although a case in which three plates 421 to 423 are displayed in the plate display area 420 is illustrated as an example in FIG. 4, the data processing apparatus may display four or more plates in the plate display area 420.

An add icon 430 may be displayed in the plate display area 420. When the add icon 430 is selected by the user, the data processing apparatus may additionally display an area in which a plate may be displayed. For example, in a case in which the first to third plates 421 to 423 are displayed in FIG. 4, when the user selects the add icon 430, the data processing apparatus may display an area, in which a fourth plate may be displayed, below the third plate. Although the add icon 430 is displayed as a figure in FIG. 4, the add icon 430 may be displayed as a box including a text, such as "add."

The data processing apparatus identifies the reaction wells selected by the user and displays the amplification data in the integrated data display area 410. The first reaction well selected by the user is the C2 well of the first plate 421, and the second reaction well selected by the user is the B5 well of the second plate 422.

The wells selected by the user may be automatically displayed in the integrated data display area 410. In addition, the user may drag and drop the C2 well of the first plate 421 and the B5 well of the first plate 422 to the integrated data display area 410.

The data processing apparatus recognizes the drag and drop and displays the amplification data of the C2 well and the B5 well in the integrated data display area 410. The graph shown in the integrated data display area 410 exhibits a data set or an amplification curve of the C2 well and the B5 well. The table shown in the integrated data display area 410 may exhibit Ct values, RFU values, or the like of the C2 well and the B5 well. When the amplification data of the reaction wells selected by the user are exhibited, the plates including the reaction wells, respectively, may be exhibited together. For example, the plates including the selected reaction wells are exhibited in a "plate" block of the table in the integrated data display area 410.

The user may designate a plurality of wells in the plates in an area designating manner, and the data processing apparatus may integrate the amplification data of the reaction wells included in the designated area and display the integrated amplification data in the integrated data display area 410.

The data processing apparatus may display the amplification data of the plates in an integrated data display area 1010 in accordance with selection criteria or sorting criteria. The selection criteria or sorting criteria may be set by default or preset by the user.

The integrated data may be displayed in the form of a graph and/or a table.

Figure 5:
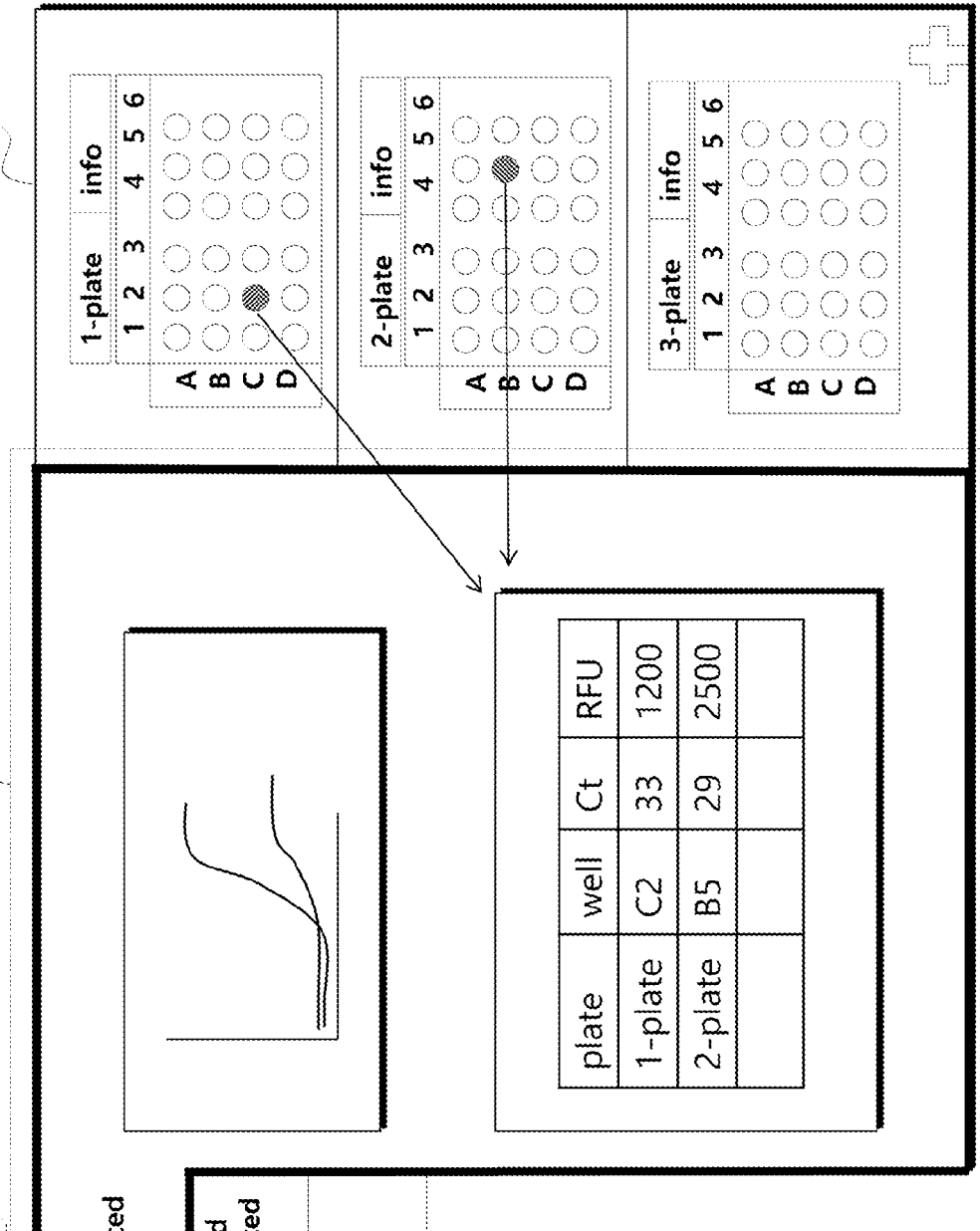
FIGS. 5 and 6 illustrate a method of displaying a plurality of pieces of integrated data using the first GUI, by which the amplification data display method according to an embodiment is performed.
Figure 6:
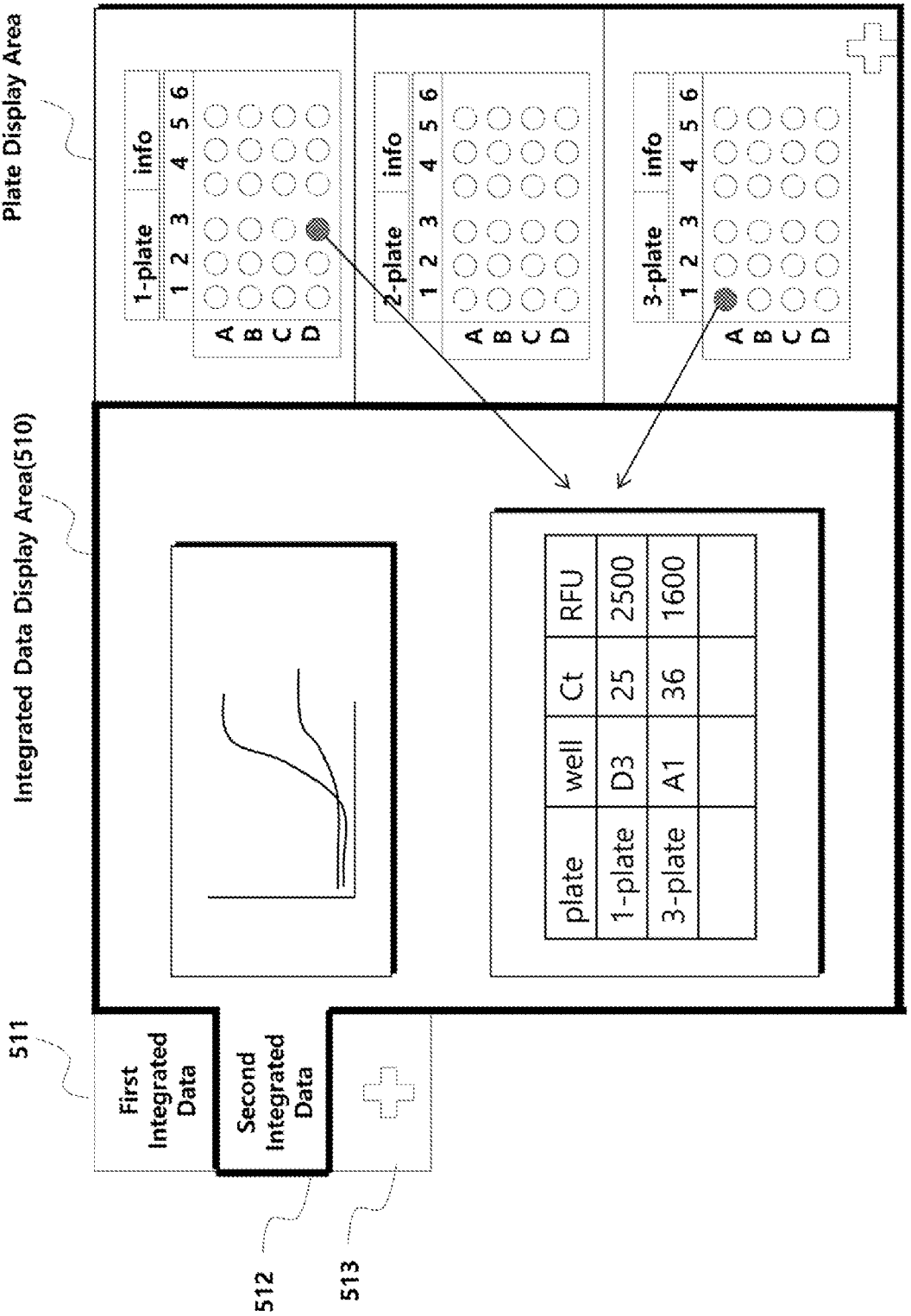

FIGS. 5 and 6 illustrate a method of displaying a plurality of pieces of integrated data using the first GUI, by which the amplification data display method according to an embodiment is performed. FIG. 5 illustrates a screen on which first integrated data 511 are displayed, and FIG. 6 illustrates a screen on which second integrated data 512 are displayed. The integrated data currently displayed in FIGS. 5 and 6 are indicated with thick lines. Any piece of integrated data to be displayed is determined by the selection of the user. The data processing apparatus may display a plurality of pieces of integrated data using sub-tabs. The data processing apparatus identifies a sub-tab selected by the user and displays integrated data corresponding to the selected sub-tab. FIG. 5 illustrates a situation in which a sub-tab indicating the first integrated data 511 is selected.

FIG. 5 illustrates an example of displaying the amplification data of the C2 well of the first plate and the amplification data of the B5 well of the second plate as the first integrated data 511. FIG. 6 illustrates an example of displaying the amplification data of the D3 well of the first plate and the A1 well of the third plate as the second integrated data 512. As illustrated in FIGS. 5 and 6, the first integrated data and the second integrated data may include the amplification data of different reaction wells.

An add icon 513 is an icon for displaying another integrated data. When the user selects the add icon 513, a sub-tab for displaying third integrated data are created. Although the add icon 513 is displayed as a figure in FIGS. 5 and 6, the add icon 513 may be displayed as a box including a text, such as "add."

Figure 7:
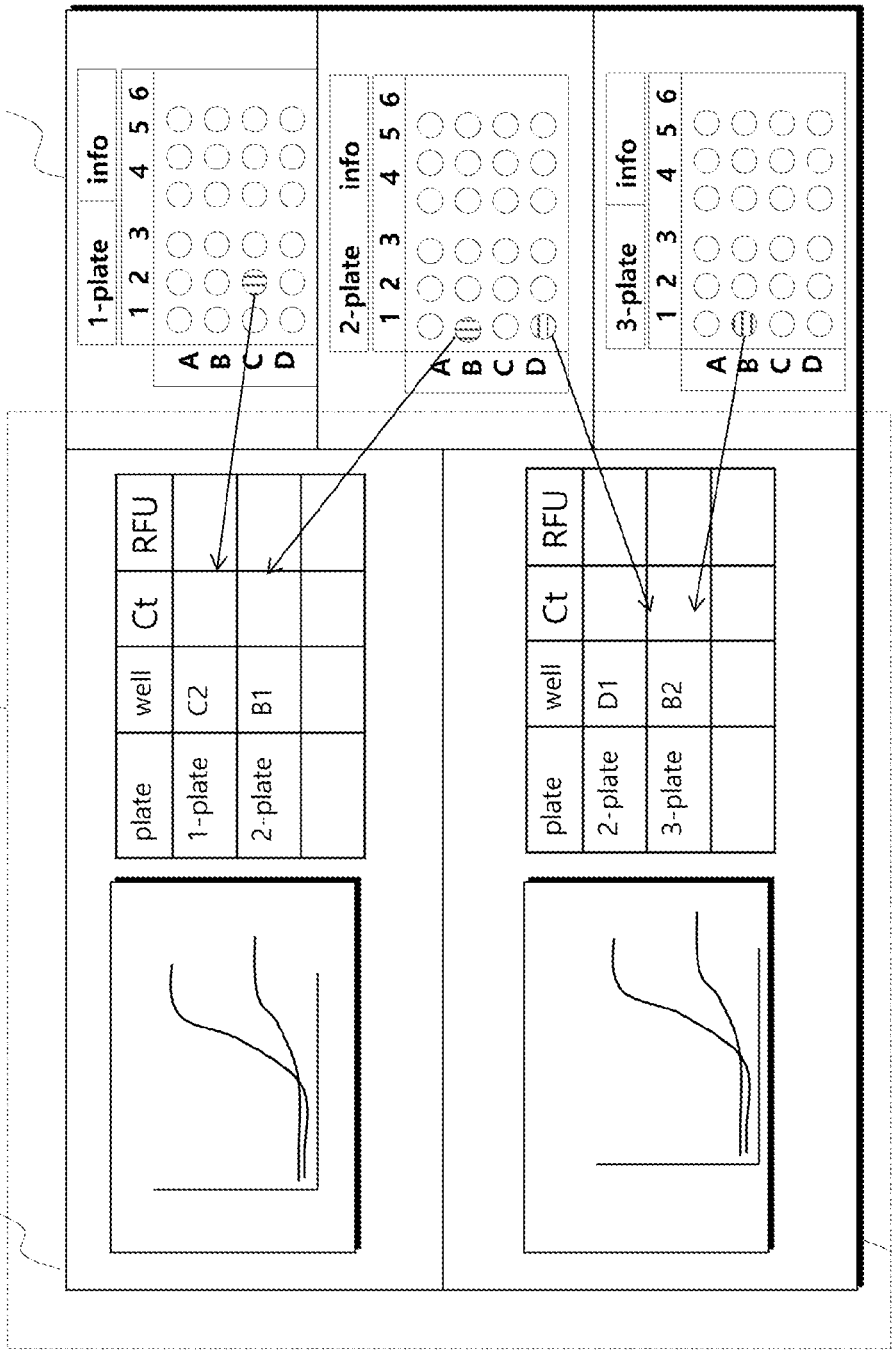
FIG. 7 is a diagram illustrating a method of displaying a plurality of pieces of integrated data using the first GUI, by which the amplification data display method according to an embodiment is performed.

FIG. 7 is a diagram illustrating a method of displaying a plurality of pieces of integrated data using the first GUI, by which the amplification data display method according to an embodiment is performed. FIG. 7 illustrates an example of displaying first integrated data 711 and second integrated data 712 in a single screen. Although the first integrated data 511 and the second integrated data 512 are illustrated using different sub-tabs in FIGS. 5 and 6, FIG. 7 is an example in which the first integrated data 711 and the second integrated data 712 are disposed in the top and bottom portions of the same screen.

In FIG. 7, the amplification data of the C2 well of the first plate and the amplification data of the B1 well of the second plate are displayed in the first integrated data 711. In the second integrated data 12, the amplification data of the D1 well of the second plate and the amplification data of the B2 well of the third plate are displayed.

In a case in which two or more pieces of integrated data are displayed together in the single screen as in FIG. 7, the user may review the amplification data displayed in an integrated data area 710. Although the first integrated data 711 is displayed in the top portion of the screen and the second integrated data 712 is displayed in the bottom portion of the screen in FIG. 7, the first integrated data 711 may be displayed in the left portion of the screen and the second integrated data 712 may be displayed to the right of the first integrated data 711. Although an example in which two integrated data 712 and 712 are displayed has been described with reference to FIG. 7, the integrated data display area may include three or more pieces of integrated data.

Reaction wells displayed in different pieces of integrated data may be distinguished by different colors, patterns, shapes, or the like. For example, reaction wells displayed in the first integrated data 711 may be displayed blue, and reaction wells displayed in the second integrated data 712 may be displayed red. In addition, as illustrated in FIG. 7, the reaction wells displayed in the first integrated data 711 may be displayed as a vertical pattern, while the reaction wells displayed in the second integrated data 712 may be displayed as a horizontal pattern.

A plurality of pieces of integrated data parts are displayed in the integrated data display area in a single screen, selected reaction wells may be located in an intended integrated data part in a drag and drop manner.

Figure 8:
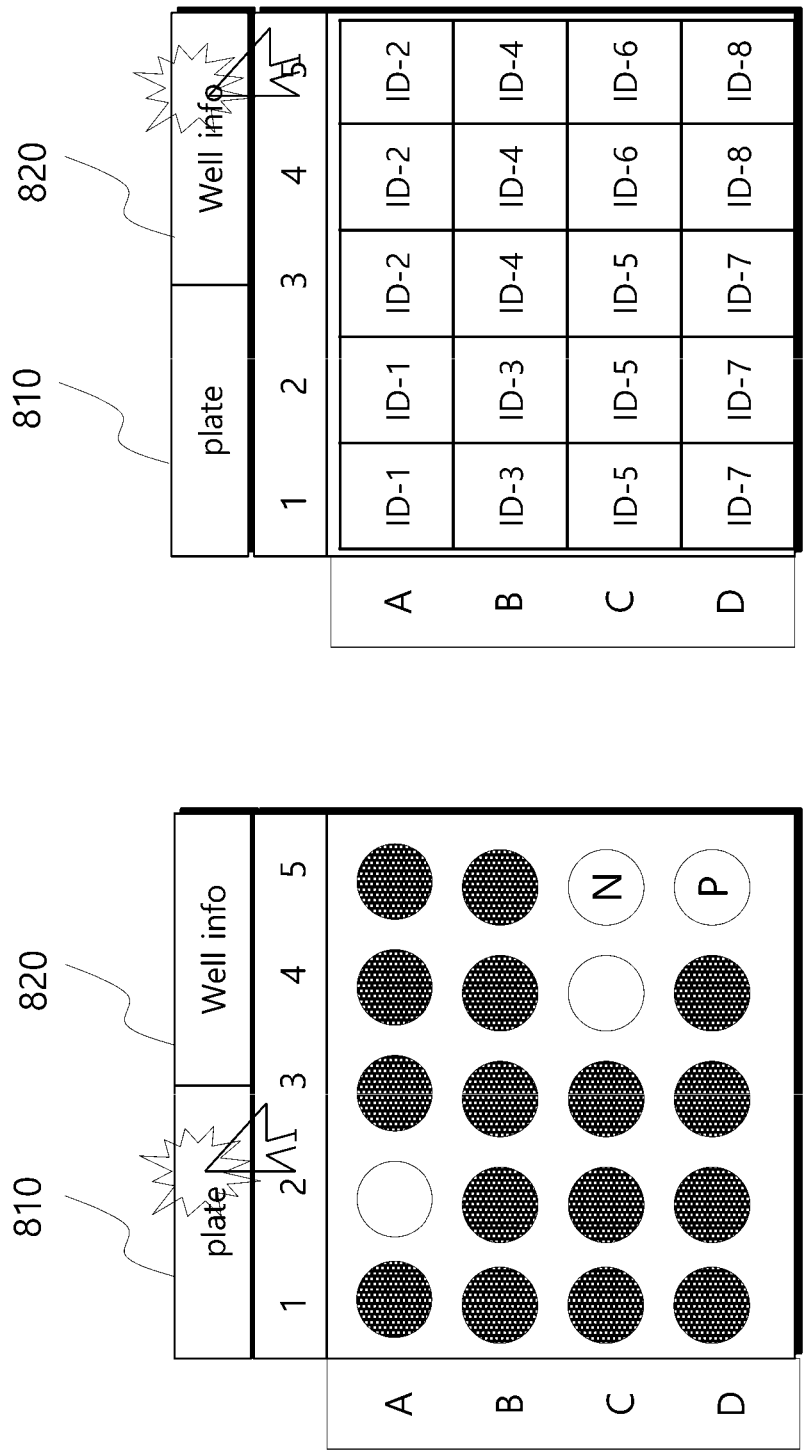
FIG. 8 is a view illustrating a method of displaying plates according to an embodiment.

FIG. 8 is a view illustrating a method of displaying plates according to an embodiment. Referring to FIG. 8, the data processing apparatus may display reaction wells included in the plates in a variety of methods. The data processing apparatus may display the result of amplification reactions, display the characteristics of reaction wells, or display user input information regarding the reaction wells.

In a case in which the user selects a plate 810, the data processing apparatus may display the positive/negative detection results of reaction wells. For example, black reaction wells indicate negative reaction wells, while white reaction wells indicate positive reaction wells. The data processing apparatus may not only display reaction wells positive or negative, but also may display reaction wells including a negative control with N and display reactions wells including a positive control with P.

In a case in which the user selects well information 820, the data processing apparatus may display identification information input regarding reaction wells. The data processing apparatus may display a text indicating patient identification information (patient ID), sample numbers, concentrations, target pathogens, types of detection signal provision labels, and the like. For example, numbers from 1 to 8 described in the positions of the reaction wells may be numbers by which patients are identified. The data processing apparatus may indicate reaction wells regarding a single patient with the same number. For example, when amplification reactions for eight patients have been performed, two reaction wells marked with ID-1 may indicate a first patient, and three reaction wells marked with ID-2 may indicate a second patient. Although a case in which patients are identified has been described as an example with reference to FIG. 8, the text displayed in the well information 820 may be designated by the user, and a plurality of pieces of information may be displayed.

Figure 9:
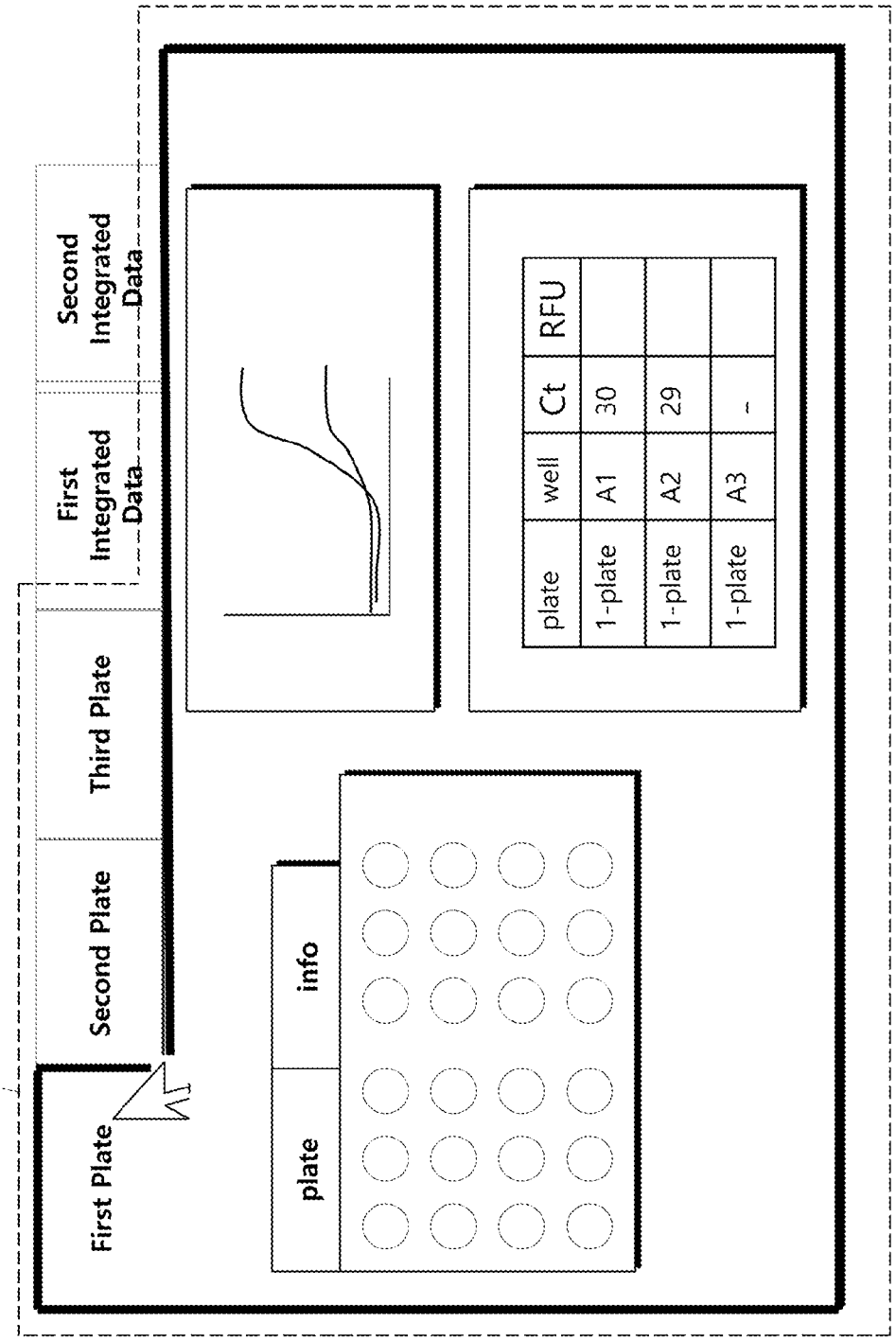

FIGS. 9 and 10 are diagrams illustrating a second graphic user interface (GUI), by which the amplification data display method according to an embodiment is performed, and the amplification data display method using the second GUI.

FIG. 9 is a diagram illustrating a method of displaying plates using the second GUI, by which the amplification data display method is performed.

Referring to FIG. 9, the data processing apparatus may use sub-tabs to display a plurality of plates in different sub-tabs.

In FIG. 9, a plate display area 910 is an area indicated with dotted lines. An area indicated with thick solid lines is plates displayed on the current screen. In FIG. 9, the plate display area 910 includes first to third plates, among which the first plate is displayed on the current screen. When the user selects the second plate, the second plate is displayed on the screen.

The plate display area 910 includes three sub-tabs. Although FIG. 9 illustrates only three plates using three sub-tabs, three or more sub-tabs may be displayed in the plate display area 910.

When the user selects the first plate, reaction wells of the first plate are displayed with icons, or amplification data regarding the reaction wells are displayed using texts or on a graph. A plate displayed in each of the plate tabs may be predetermined or may be selected directly from each tab. The user may select reaction wells, the amplification data of which are intended to be displayed.

Information regarding the reaction wells may be displayed on the icons using colors, texts, or the like. A data set of the reaction wells is displayed on the graph, and data, such as Ct values or RUF values, of the reaction wells are displayed on the table.

FIG. 10 is diagram illustrating the method of displaying the amplification data using the second GUI, by which the amplification data display method according to an embodiment is performed. Referring to FIG. 10, the data processing apparatus may display a plurality of pieces of integrated data using the sub-tabs. In addition, the data processing apparatus may display the amplification data of the plates in the integrated data display area 1010.

Although FIG. 10 illustrates a case in which first and second integrated data are displayed as an example, the data processing apparatus may display a single piece of integrated data or three or more pieces of integrated data. The integrated data includes amplification data included in one or more plates.

In FIG. 10, the integrated data display area 1010 is an area indicated with dotted lines. An area indicated with thick solid lines is integrated data displayed on the current screen. FIG. 10 illustrates the first integrated data, and the amplification data sorted on the basis of the patient IDs are displayed. In case of the same patient ID, the amplification data are sorted on the basis of the plates.

Since the first to third plates are selected by the user, the data processing apparatus may display the amplification data included in the first to third plates. That is, when the user selects the plates, data processing apparatus may automatically identifies the selected plates and display the amplification data included in the selected plates.

According to an implementation, the data processing apparatus sets selection criteria (or sorting criteria). The selection criteria (or sorting criteria) may be set by the user or be set by default. The data processing apparatus may display only the amplification data of the reaction wells, selected in accordance with the set selection criteria, in the integrated data display area 1010. In addition, the data processing apparatus may display the amplification data of the reaction wells in the integrated data display area 1010, sorted in accordance with the set sorting criteria. For example, the data processing apparatus may display the amplification data by sorting the amplification data by a sorting method using the identification information of the reaction wells.

The data processing apparatus displays the amplification data in accordance with the selection criteria (or sorting criteria). For example, the data processing apparatus may display the amplification data of the reaction wells, selected from the plurality of plates in accordance with the selection criteria, as the first integrated data. The data processing apparatus may display the amplification data, additionally sorted in accordance with the sorting criteria, as the first integrated data. In another example, the data processing apparatus may display the amplification data, obtained by sorting the amplification data of the reaction well of all of the elected pats in accordance with the sorting criteria, as the second integrated data.

The data processing apparatus may display the amplification data selected in accordance with other selection criteria or amplification data sorted in accordance with other sorting criteria as the third integrated data.

The amplification data that the data processing apparatus selects in accordance with the selection criteria or sorts in accordance with sorting criteria are the amplification data included in the reaction wells of the plates selected by the user. That is, the data processing apparatus displays the amplification data included in the plates selected by the user from the current window (i.e. the plates displayed in the current window) in the integrated data. In a case in which the selection criteria or the sorting criteria are preset, the data processing apparatus may automatically generate and display the integrated data only by an operation of the user selecting the plate.

The user may determine the selection criteria of the amplification data displayed in the integrated data. For example, the user may determine the selection criteria using the reaction well identification information, such as unique numbers of reaction wells, patient identification information (patient ID), sample numbers, concentrations, target pathogens, types of detection signal provision labels, which may be used to identify the reaction well in the plates; the plate identification information, such as plate numbers, used to identify the plates; or the amplification data information, such as Ct values of reaction wells and positive/negative results.

The data processing apparatus displays the amplification data in accordance with the selection criteria determined by the user. For example, in a case in which the user selects 001 as the patient ID, the data processing apparatus collects only the amplification data, the patient ID of which is 001, and displays the collected amplification data as the integrated data.

The user may determine the selection criteria of the amplification data displayed in the first integrated data. For example, the user may determine the selection criteria using the reaction well identification information, such as unique numbers of reaction wells, patient identification information (patient ID), sample numbers, concentrations, target pathogens, types of detection signal provision labels, which may be used to identify the reaction well in the plates; the plate identification information, such as plate numbers, used to identify the plates; or the amplification data information, such as Ct values of reaction wells and positive/negative results. For example, when the user determines the patient ID as the selection criteria, the data processing apparatus may display the amplification data, sorted on the basis of the patient IDs.

The selection criteria or the sorting criteria may be set by default. The default is the preset selection or sorting criteria, instead of being specifically designated by the user. For example, all of the plates may be set by the default of the selection criteria. In addition, a reaction well using a specific type of detection label or a reaction well used for detection of a specific pathogen may be set by the default of the selection criteria. In addition, the patient ID may be set by the default of the sorting criteria. In this case, the amplification data are sorted on the basis of the patient IDs without a user input. In a case in which the amplification data are sorted on the basis of the patient IDs or the sample numbers, the data processing apparatus displays the amplification data, corresponding to the same patient ID or the same sample number included in the plates, in adjacent positions on the table. In a case in which the amplification data are sorted on the basis of the concentrations, the data processing apparatus may sort the amplification data in order from the lower concentration to the higher concentration or from the higher concentration to the lower concentration. In a case in which the amplification data are sorted on the basis of the plate numbers, the data processing apparatus displays the amplification data having the same plate number in adjacent positions on the table. In a case in which the amplification data are sorted on the basis of the wells, the amplification data are aligned in accordance with the positions of the reaction wells. For example, the data processing apparatus A3 well of the first plate, A3 well of the second plate, and A3 well of the third plate in adjacent positions on the table. In a case in which the amplification data are sorted on the basis of the Ct values, the data processing apparatus sorts the amplification data in order from the lower Ct value to the higher Ct value or from the higher Ct value to the lower Ct value. In a case in which the amplification data are sorted on the basis of the positive/negative results, the data processing apparatus displays the amplification data of the positive reaction wells in adjacent positions on the table and displays the amplification data of the negative reaction wells in adjacent positions on the table.

The data processing apparatus may displays the amplification data, sorted on the basis of two or more sorting criteria. For example, in a case in which the amplification data are sorted on the basis of the positive/negative results and the Ct values, the data processing apparatus may sort the positive amplification data in order from the higher Ct value to the lower Ct value. In the case of FIG. 10, the amplification data are sorted on the basis of the IDs and the plates. Thus, the data processing apparatus sorts the amplification data in order of the IDs, and in case of the same ID, sorts the amplification data in order of the plates.

Alternatively, the amplification data of the reaction wells selected by the user may be displayed in the integrated data display area 1010.

Figure 11:
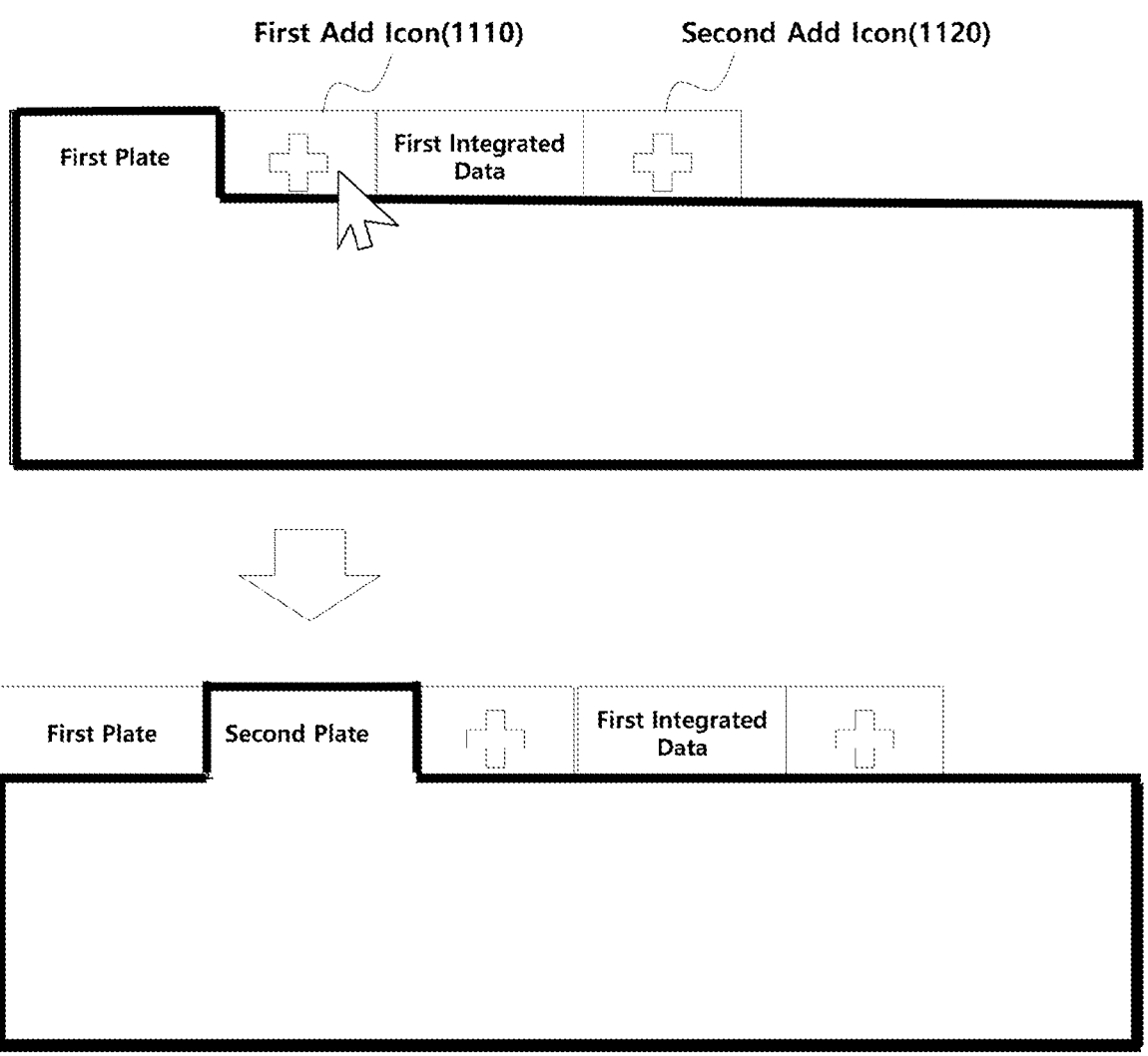
FIG. 11 is a diagram illustrating a method of adding a plate using the second GUI, by which the amplification data display method according to an embodiment is performed.

FIG. 11 is a diagram illustrating a method of adding a plate using the second GUI, by which the amplification data display method according to an embodiment is performed. A first add icon 1110 is an icon used to add a plate, while a second add icon 1120 is an icon used to add integrated data. Thick solid lines indicate a plate displayed on the current screen. The upper window displays a first plate with thick solid lines, while the lower window displays a second plate with thick solid lines.

FIG. 11 illustrates a situation in which the second plate when the user has selected the first add icon 1110. The second plate is generated to the right of the first plate. The data processing apparatus may display only the amplification data included in the displayed plates as the integrated data.

Figure 12:
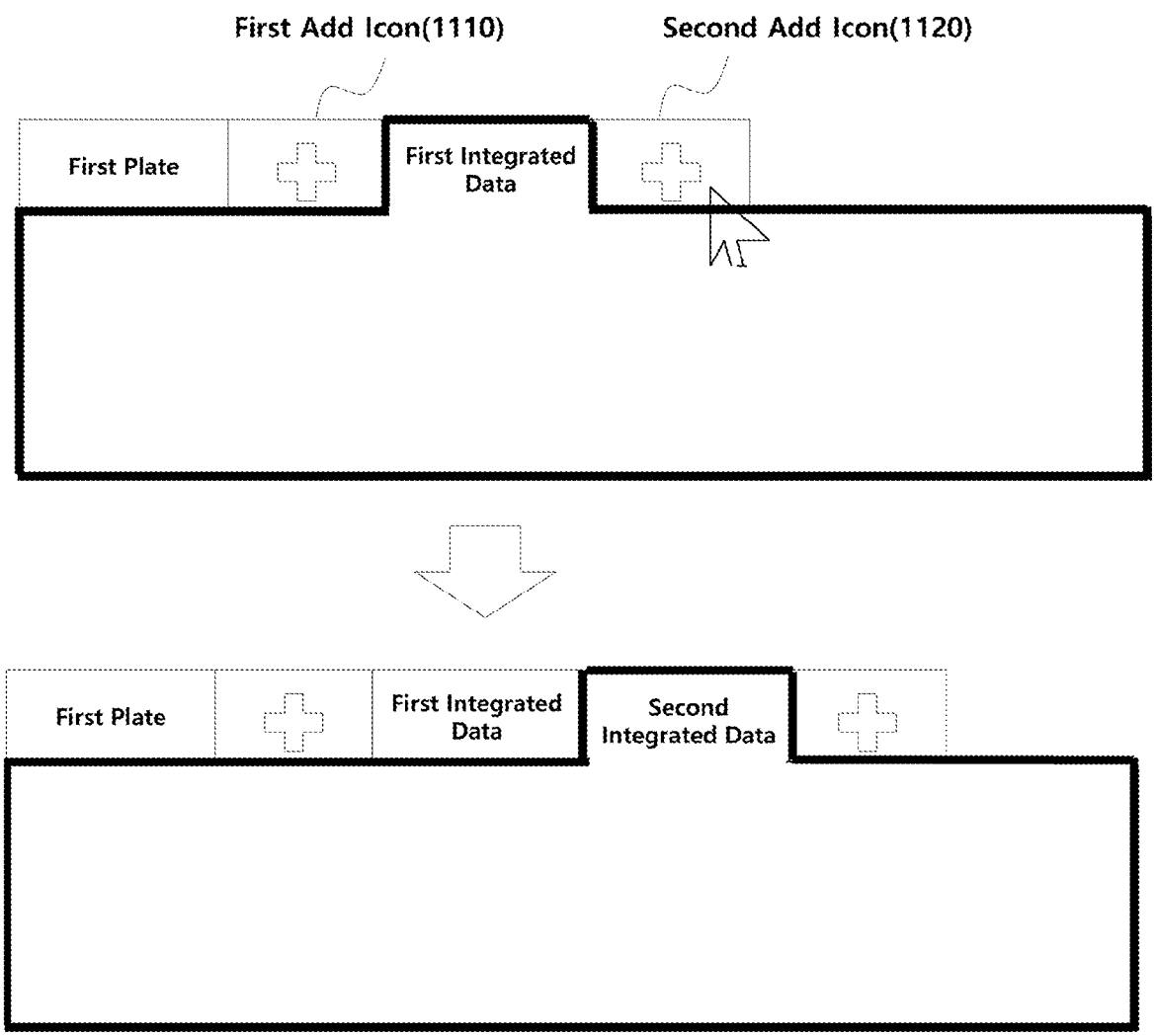
FIG. 12 is a diagram illustrating a method of adding integrated data using the second GUI, by which the amplification data display method according to an embodiment is performed.

FIG. 12 is a diagram illustrating a method of adding integrated data using the second GUI, by which the amplification data display method according to an embodiment is performed. FIG. 12 illustrates a situation in which the second integrated data are added when the user has selected the second add icon 1120. The second integrated data is generated to the right of the first integrated data. The data processing apparatus may display the amplification data in accordance with the selection criteria or sorting criteria regarding the second integrated data.

As the specific parts of the present disclosure have been described in detail hereinabove, those having ordinary knowledge will appreciate that such specific parts are example embodiments only and the scope of the present disclosure is not limited thereto. Therefore, the practical scope of the present disclosure shall be defined by the appended claims and equivalents thereof.

The invention claimed is:

1. A method of displaying amplification data generated by nucleic acid amplification reactions, the method comprising:
displaying a plate display area and an integrated data display area, wherein the plate display area displays plates in which nucleic acid amplification reactions have been performed, and the integrated data display area displays amplification data, wherein the plate display area and the integrated data display area are simultaneously displayed on one screen;
displaying two or more different plates simultaneously in the plate display area, wherein each of the plates includes a plurality of reaction wells, and the amplification data are generated from the reaction wells by the nucleic acid amplification reactions, the reaction wells being displayed on the plate as icons selectable by a user;

receiving user inputs that select a first icon of a first reaction well of a first plate of the two or more different plates simultaneously displayed in the plate display area, and select a second icon of a second reaction well of a second plate of the two or more different plates simultaneously displayed in the plate display area; and displaying the amplification data of the plurality of reaction wells including the first reaction well and the second reaction well, in the integrated data display area, wherein the integrated data display area comprises a first integrated data display area and a second integrated data display area, wherein the first integrated data display area includes amplification curve lines corresponding to (i) the first icon of the first reaction well of the first plate and (ii) the second icon of the second reaction well of the second plate, and the second integrated data display area includes at least one from among a signal value, a positive/negative result, and a cycle threshold value, corresponding to (i) the first icon of the first reaction well of the first plate and (ii) the second icon of the second reaction well of the second plate, and wherein the first integrated data display area and the second integrated data display area are simultaneously displayed.

2. The method according to claim 1, wherein the user inputs comprise an operation of dragging and dropping a particular reaction well from the two or more different plates simultaneously displayed in the plate display area, to the integrated data display area.

3. The method according to claim 1, wherein the displaying the amplification data comprises:
displaying the amplification data of the plurality of reaction wells, in accordance with set selection criteria, on at least one of a graph and a table.

4. The method according to claim 1, wherein the displaying the amplification data comprises:
sorting the amplification data by a sorting method using identification information of the plurality of reaction wells; and
displaying a result of the sorting.

5. The method according to claim 1, wherein images of the two or more different plates are displayed in the plate display area, and the plurality of reaction wells in the plates are displayed as icons or using texts indicating identification information regarding the plurality of reaction wells.

6. The method according to claim 1, wherein the amplification data include at least one from among a set of cycle numbers and signal values, a signal value in a specific cycle, a positive/negative result, and a cycle threshold value.

7. The method according to claim 1, wherein the plate display area includes an icon used to add a plate to be displayed, or the integrated data display area includes an icon used to add displaying of other amplification data.

8. The method according to claim 1, wherein the amplification data comprises:
a table showing first amplification data corresponding to the first reaction well, and also showing a second amplification data corresponding to the second reaction well.

9. An apparatus for displaying amplification data generated by nucleic acid amplification reactions, the apparatus comprising:
a memory;
a display apparatus; and
a processor,
wherein the processor controls the display apparatus to display a plate display area and an integrated data display area on the display apparatus, wherein the plate display area displays plates in which nucleic acid amplification reactions have been performed, and the integrated data display area displays amplification data, wherein the plate display area and the integrated data display area are simultaneously displayed on one screen of the display apparatus;

the processor controls the display apparatus to display two or more different plates simultaneously in the plate display area on the display apparatus, wherein each of the plates includes a plurality of reaction wells, and the amplification data are generated from the reaction wells by the nucleic acid amplification reactions, the reaction wells being displayed on the plate as icons selectable by a user;

the processor receives user inputs that select a first icon of a first reaction well of a first plate of the two or more different plates simultaneously displayed in the plate display area, and select a second icon of a second reaction well of a second plate of the two or more different plates simultaneously displayed in the plate display area; and the processor controls the display apparatus to display the amplification data of the plurality of reaction wells including the first reaction well and the second reaction well, in the integrated data display area, on the display apparatus, wherein the integrated data display area comprises a first integrated data display area and a second integrated data display area, wherein the first integrated data display area includes amplification curve lines corresponding to (i) the first icon of the first reaction well of the first plate and (ii) the second icon of the second reaction well of the second plate, and the second integrated data display area includes at least one from among a signal value, a positive/negative result, and a cycle threshold value corresponding to (i) the first icon of the first reaction well of the first plate and (ii) the second icon of the second reaction well of the second plate, and wherein the first integrated data display area and the second integrated data display area are simultaneously displayed.

10. The apparatus according to claim 9, wherein the user inputs comprise an operation of dragging and dropping a particular reaction well from the two or more different plates simultaneously displayed in the plate display area, to the integrated data display area.

11. The apparatus according to claim 9, wherein the processor controls the display apparatus to display the amplification data of the plurality of reaction wells, in accordance with set selection criteria, on at least one of a graph and a table.

12. The apparatus according to claim 9, wherein the processor sorts the amplification data by a sorting method using identification information of the plurality of reaction wells, and display a result of the sorting.

13. The apparatus according to claim 9, wherein images of the two or more different plates are displayed in the plate display area, and the plurality of reaction wells in the plates are displayed as icons or using texts indicating identification information regarding the plurality of reaction wells.

14. The apparatus according to claim 9, wherein the amplification data include at least one from among a set of cycle numbers and signal values, a signal value in a specific cycle, a positive/negative result, and a cycle threshold value.

15. The apparatus according to claim 9, wherein the plate display area includes an icon used to add a plate to be displayed, or the integrated data display area includes an icon used to add displaying of other amplification data.

16. The apparatus according to claim 9, wherein the processor displays the amplification data in a form of a table showing first amplification data corresponding to the first reaction well, and also showing a second amplification data corresponding to the second reaction well.

17. A non-transitory recording medium storing a computer executable program, wherein the program comprises:
  displaying a plate display area and an integrated data display area, wherein the plate display area displays plates in which nucleic acid amplification reactions have been performed, and the integrated data display area displays amplification data, wherein the plate display area and the integrated data display area are simultaneously displayed on one screen;
  displaying two or more different plates simultaneously in the plate display area, wherein each of the plates includes a plurality of reaction wells, and the amplification data are generated from the reaction wells by the nucleic acid amplification reactions, the reaction wells being displayed on the plate as icons selectable by a user;
  receiving user inputs that select a first icon of a first reaction well of a first plate of the two or more different plates simultaneously displayed in the plate display area, and select a second icon of a second reaction well of a second plate of the two or more different plates simultaneously displayed in the plate display area; and
  displaying the amplification data of the plurality of reaction wells including the first reaction well and the second reaction well, in the integrated data display area,
  wherein the integrated data display area comprises a first integrated data display area and a second integrated data display area,
  wherein the first integrated data display area includes amplification curve lines corresponding to (i) the first icon of the first reaction well of the first plate and (ii) the second icon of the second reaction well of the second plate, and
  the second integrated data display area includes at least one from among a signal value, a positive/negative result, and a cycle threshold value corresponding to (i) the first icon of the first reaction well of the first plate and (ii) the second icon of the second reaction well of the second plate, and
  wherein the first integrated data display area and the second integrated data display area are simultaneously displayed.

* * * * *